United States Patent [19]

Takayanagi et al.

[11] Patent Number: 5,118,827
[45] Date of Patent: Jun. 2, 1992

[54] MONOCYCLIC TERPENE DERIVATIVES

[75] Inventors: Hisao Takayanagi; Yasunori Kitano, both of Yokohama; Yasuhiro Morinaka, Tsuchiura, all of Japan

[73] Assignee: Mitsubishi Kasei Corporation, Tokyo, Japan

[21] Appl. No.: 555,999

[22] Filed: Jul. 16, 1990

[30] Foreign Application Priority Data

Jul. 14, 1989 [JP] Japan .................................. 1-181709
Jul. 14, 1989 [JP] Japan .................................. 1-181710
Dec. 20, 1989 [JP] Japan .................................. 1-330258

[51] Int. Cl.$^5$ ................................. C07F 7/10
[52] U.S. Cl. ................................. 556/415; 558/303; 558/315
[58] Field of Search ................. 556/415; 558/315, 303

[56] References Cited

U.S. PATENT DOCUMENTS 4,360,467 11/1982 Kanojia ............................ 556/415 X

FOREIGN PATENT DOCUMENTS 0408053 1/1991 European Pat. Off. .
1814873 7/1969 Fed. Rep. of Germany .

OTHER PUBLICATIONS

Takayanagi et al., Tetrahedron Letters, vol. 31, No. 23, pp. 3317–3320 (1970).
McMurry et al., Chem. Abstr., vol. 112(1) 7748q.

*Primary Examiner*—Paul F. Shaver
*Attorney, Agent, or Firm*—Wenderoth, Lind & Ponack

[57] ABSTRACT

Novel monocyclic terpene derivative of the formula:

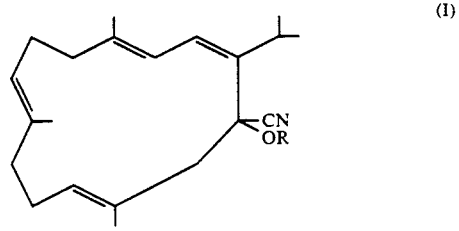

(I)

wherein R is hydrogen atom, trimethylsilyl group or 1-ethoxyethyl group, and novel intermediate therefor. The terpene derivative (I) is a useful intermediate for preparing Sarcophytol A having an anti-carcinogenesis promoter activity and an antitumor activity.

7 Claims, No Drawings

MONOCYCLIC TERPENE DERIVATIVES

The present invention relates to a novel 2-(1-methylethyl)-5,9,13-trimethyl-2,4,8,12-cyclotetradecatetraene-1-carbonitril derivative. More particularly, it relates to a novel monocyclic terpene derivative which is an important intermediate for complete synthesis of Sarcophytol A which has an anti-tumor promoter activity [Cancer Surveys, 2, 540 (1983); Taisha (metabolism), vol. 25 an extra edition, cancer '88, 3 (1988)]and an antitumor activity [Japanese Patent First Publication No. 61317/1981].

PRIOR ART

Sarcophytol A is a cembrane type macrocyclic diterpene alcohol having a special structure of 14-membered ring which contains four double bonds including one covalent double bond therein. Sarcophytol A has hitherto never been synthesized. Among the cembranoids having four double bonds in the macrocyclic ring, only sarcophytol B of the following formula has been synthesized [Tetrahedron Letters, 30, 1173 (1989)]. However, this process produces a 1,2-diol product but not a monoalcohol compound and hence cannot be applied to the synthesis of Sarcophytol A of the following formula.

Sarcophytol A

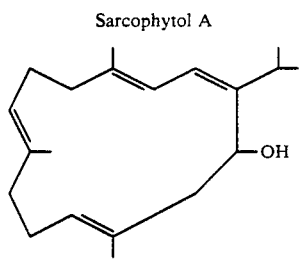

Sarcophytol B

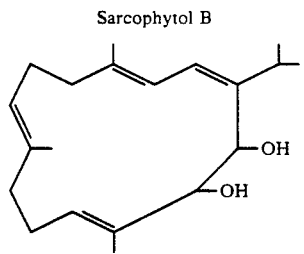

SUMMARY OF THE INVENTION

Under the circumstances, the present inventors have intensively studied as to a process for preparing Sarcophytol A, and as a result, have found that Sarcophytol A can advantageously be prepared by using a monocyclic terpene derivative of the present invention as an intermediate.

An object of the present invention is to provide a monocyclic terpene derivative which is a useful intermediate for synthesis of Sarcophytol A. This and other objects and advantages of the invention will be apparent to those skilled in the art from the following description.

DETAILED DESCRIPTION OF THE INVENTION

The monocyclic terpene derivative of the present invention has the following formula (I):

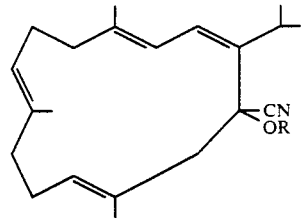

wherein R is hydrogen atom, trimethylsilyl group or 1-ethoxyethyl group.

Preferable monocyclic terpene derivatives of the present invention are as follows:

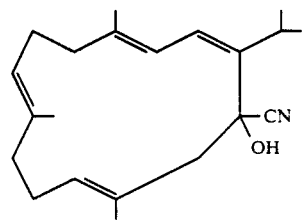

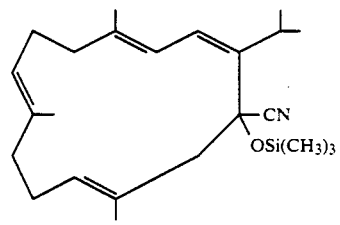

and

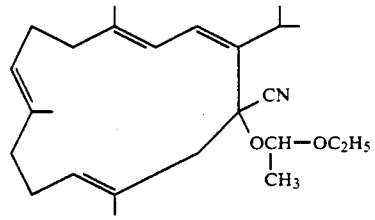

Among the compounds of the present invention, the compound of the formula (I) wherein R is a trimethylsilyl group can be prepared, for example, by a process as shown in the following reaction scheme:

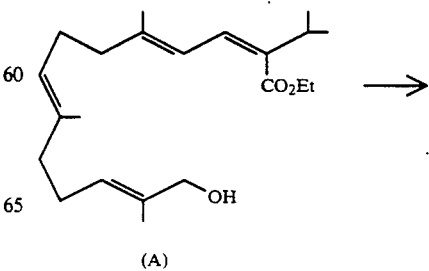

(A)

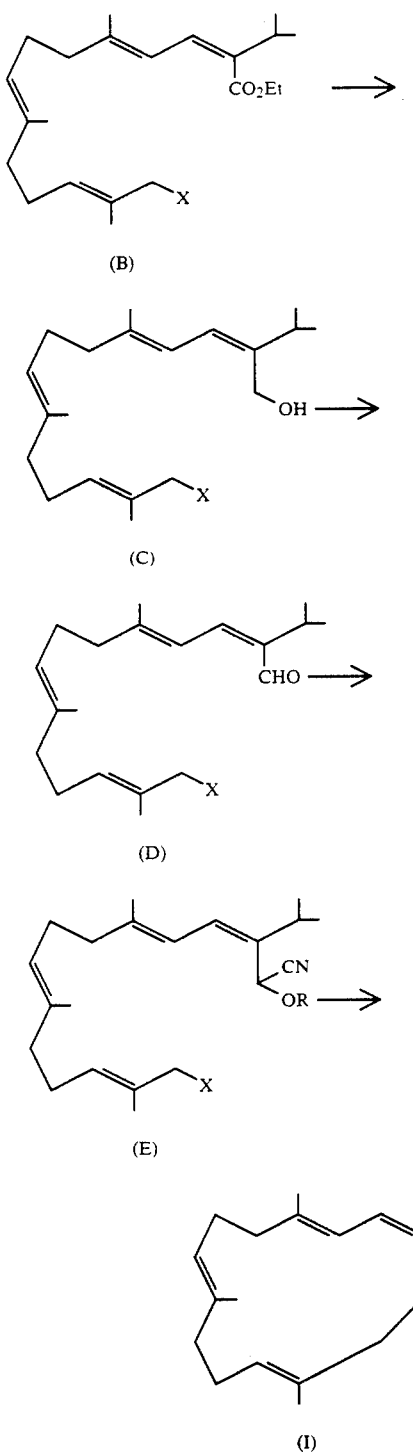

(B)

(C)

(D)

(E)

(I)

In the above reaction scheme, X represents a halogen atom or a group of the formula: —OSO₂R¹ wherein R¹ is a lower (C₁₋₄) alkyl group optionally substituted by a halogen atom or a phenyl group optionally substituted by a lower (C₁₋₄) alkyl group.

The compound (B) can be prepared from a lower alkyl ester of 14-hydroxy-2-(1-methylethyl)-5,9,13-trimethyl-2,4, 8,12-tetradecatetraenoic acid (A) which is a known compound [Tetrahedron Letters, 30, 1173 (1989)]by halogenation without an allyl rearrangement in said allyl alcohol moiety. For example, the compound (B) can be prepared by reacting the compound (A) with 1 to 10 equivalents of a carbon tetrahalide in the presence of 1 to 10 equivelents of triphenylphosphine in an inert solvent (e.g. acetonitrile etc.) or, in case of chlorination, with carbon tetrachloride which is also used as a solvent, at a temperature of from room temperature to 100° C. for 1 to 8 hours, or reacting the compound (A) with 1 to 10 equivalents of methanesulfonyl chloride, a metal halide and S-collidine in a polar aprotic solvent (e.g. dimethylformamide etc.) at a temperature of from —40° C. to room temperature for 1 to 10 hours. Alternatively, the compound (B) wherein X is —OSO₂R¹ can be prepared by reacting the above alcohol (A) with 1 to 10 equivalents of a sulfonic acid chloride (e.g. methanesulfonyl chloride, para-toluenesulfonyl chloride, etc.) or a sulfonic anhydride (e.g. trifluoromethanesulfonic anhydride, etc.) in an etheric solvent (e.g. diethyl ether, tetrahydrofuran, etc.) or a halide solvent (e.g. methylene chloride, chloroform, etc.) in the presence of 1 to 10 equivalents of an amine (e.g. triethylamine, pyridine, etc.), or in a solvent of pyridine, at a temperature of from —40° C. to room temperature for 1 to 10 hours.

The compound (C) can be prepared by reacting a lower alkyl ester of 14-substituted-2-(1-methylethyl)-5,9, 13-trimethyl-2,4,8,12-tetradecatetraenoic acid (B) prepared as above with 1 to 10 equivalents of a metal hydride (e.g. diisobutyl aluminum hydride, etc.) or a metal complex compound (e.g. lithium aluminum hydride, etc.) in an etheric solvent (e.g. diethyl ether, tetrahydrofuran, etc.), benzene, toluene, hexane, heptane or the like at a temperature of from —70° C. to 50° C. to selectively reduce the ester group of the compound (B).

The compound (D) can be prepared by reacting one part by weight of the thus prepared 14-substituted-2-(1-methylethyl) 5,9,13-trimethyl-2,4,8,12-tetradecatetraene-1-ol (C) with 5 to 20 parts by weight of an oxidizing agent (e.g. powdery manganese dioxide, barium manganate, etc.) in a halide solvent (e.g. methylene chloride, chloroform, etc.), a hydrocarbon solvent (e.g. hexane, heptane, etc.), diethyl ether, ethyl acetate or the like at a temperature of from 0° C. to 50° C. for 1 to 50 hours.

The compound (E) wherein R is a trimethylsilyl group can be prepared, for example, by reacting the 14-substituted-(1-methylethyl)-5,9,13-trimethyl-2,4,8,12-tetradecatetraenal (D) with 1 to 10 equivalents of trimethylsilylnitrile in the presence of a catalytic amount of metal cyanide 18-crown-6-ether complex in a solvent (e.g. methylene chloride, chloroform, ethyl acetate, etc.) or without a solvent at a temperature of from —20° C. to 50° C. for 30 minutes to 5 hours. The corresponding cyanohydrin compound, the compound (E) wherein R is hydrogen atom, i.e. 15-substituted-2-hydroxy-3-(1-methylethyl)-6,10,14-tri-methyl-3,5,9,13-pentadecatetraenenitrile, can be prepared by dissolving the compound (E) wherein R is trimethylsilyl group in a solvent (e.g. tetrahydrofuran, methanol, etc.), and treating the solution with an aqueous mineral acid solution (e.g. 0.1 to 3 N hydrochloric acid, sulfuric acid, etc.) at a temperature of from 0° C. to room temperature for 5 minutes to 5 hours, or by reacting the compound (E) wherein R is trimethylsilyl group with a catalytic amount to 10 equivalents of a tetraalkylammonium compound (e.g. tetrabutylammonium fluoride, etc.) in a solvent (e.g. tetrahydrofuran, dioxane, etc.) at a temperature of from −20° C. to room temperature. The compound (E) wherein R is 1-ethoxyethyl group can be prepared by reacting the above cyanohydrin compound with 1 to 10 equivalents of ethyl vinyl ether in the presence of a catalytic amount of a mineral acid (e.g. hydrochloric acid, sulfuric acid, etc.) or a strong organic acid (e.g. para-toluenesulfonic acid, etc.) in a solvent (e.g. ethyl ether, ethyl acetate, etc.) at a temperature of from −20° C. to room temperature for 30 minutes to 5 hours.

Finally, the compound (E) wherein R is trimethylsilyl group or 1-ethoxyethyl group is reacted with 1 to 10 equivalents of a base (e.g. lithium diisopropylamide, lithium bis(trimethylsilyl) amide, sodium hydride, etc.) in an etheric solvent (e.g. ethyl ether, tetrahydrofuran, etc.), an aromatic hydrocarbon solvent (benzene, toluene, etc.) or a saturated hydrocarbon solvent (e.g. n-hexane, n-heptane, etc.) at a temperature of from −70° C. to 100° C. for 5 minutes to 10 hours to give the desired compound (I) of the present invention wherein R is trimethylsilyl group or 1-ethoxyethyl group, which is further converted into the other desired compound (I) of the present invention wherein R is hydrogen atom by treating it with an aqueous mineral acid solution (e.g. 0.1 to 1 N hydrochloric acid, sulfuric acid, etc.) in a solvent (e.g. tetrahydrofuran, methanol, etc.) at a temperature of from 0° C. to room temperature for 5 minutes to 5 hours, or with a catalytic amount to 10 equivalents of a tetraalkylammonium compound (e.g. tetrabutylammonium fluoride, etc.) in a solvent (e.g. tetrahydrofuran, dioxane, etc.) at a temperature of from −20° C. to room temperature.

The compound (I) of the present invention as prepared above can be converted into Sarcophytol A useful as an anti-tumor promoter and an antitumor agent, for example, by a process as shown in the following reaction scheme:

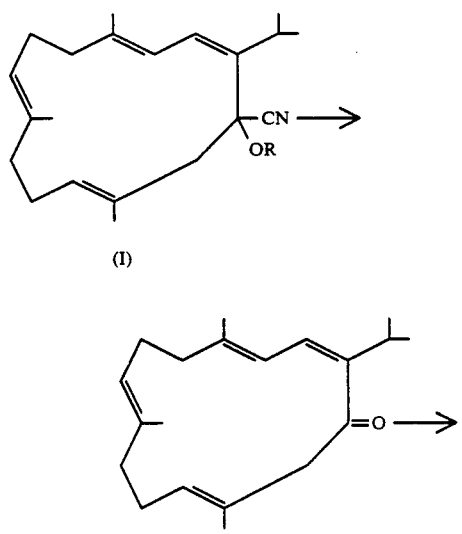

(I)

-continued

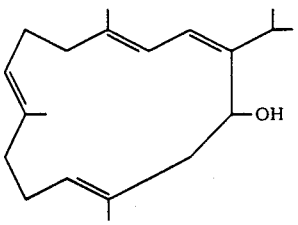

Sarcophytol A

Firstly, the compound (I) of the present invention wherein R is hydrogen atom is easily converted into the corresponding ketone, 2-(1-methylethyl)-5,9,13-trimethyl-2, 4,8,12-cyclotetradecatetraen-1-one, by dissolving the compound (I) wherein R is hydrogen atom in an organic solvent (e.g. diethyl ether, ethyl acetate, etc.) and treating the solution with an aqueous sodium hydrogen carbonate or sodium hydroxide solution at a temperature of from 0° C. to room temperature for 5 minutes to 5 hours. The ketone is also obtained by heating directly the compound (I) of the present invention wherein R is a trimethylsilyl group with a catalytic amount to 10 equivalents of tetraalkylammonium compound (e.g. tetrabutylammonium fluoride, etc.) in an aqueous organic solvent (e.g. tetrahydrofuran, dioxane, etc.). The ketone is then reacted with 1 to 10 equivalents of a reducing agent such as a metal hydride (e.g. diisobutylaluminum hydride, etc.) or a metal hydride complex (e.g. lithium aluminum hydride, etc.) in an etheric solvent (e.g. diethyl ether, tetrahydrofuran, etc.), an aromatic hydrocarbon solvent (e.g. benzene, toluene, etc.) or a saturated hydrocarbon solvent (e.g. n-hexane, n-heptane, etc.) at −70° C. to 50° C. for 5 minutes to 5 hours to give Sarcophytol A.

In the above process of preparation of Sarcophytol A from the ketone, it is preferable to previously asymmetrically modify the metal hydride or metal hydride complex used therein as the reducing agent by treating it with an asymmetric modifier since the optically active Sarcophytol A is obtained in a high yield with a high enantioselectivity. The asymmetrically modified reducing agent is prepared by treating the metal hydride or metal hydride complex with an asymmetric modifier in the presence of an additive such as an alkyl-substituted aniline, a substituted aminopyridine, tin (I) chloride, etc. whereby the asymmetric modifier is coordinated to the metal hydride or metal hydride complex. The asymmetric modifier includes, for example, an asymmetric aminoalcohol prepared by converting the carboxyl group of an optically active amino acid (e.g. L-proline, L-valine, etc.) into a substituted alcohol group or a substituted amino group [Bull. Soc. Chim. Belg., 97, 691 (1988); J. Chem. Soc. Perkin I, 1673 (1983)], an asymmetric diamine [Bull. Chem. Soc. Japan, 51, 1869 (1978); Tetrahedron, 37, 4111 (1981)], an asymmetric alkaloid such as L- or D-methylephedrine [Chem. Pharm. Bull., 31, 837 (1983)] or (S)- or (R)-1,1'-bis-2-naphthol, and the like.

The above process is an industrially advantageous process for preparing Sarcophytol A, and hence, the compound (I) of the present invention is an extremely important intermediate for preparation thererof.

The present invention is illustrated by the following Examples in more detail, but should not be construed to be limited thereto.

EXAMPLE 1

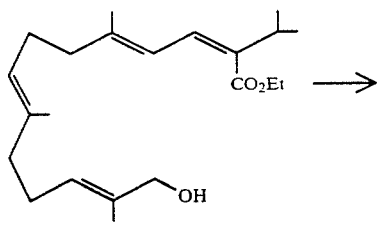

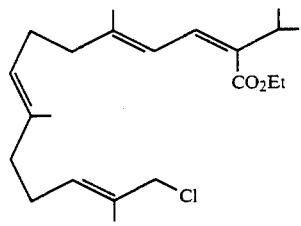

To a solution of the starting hydroxyester compound which is 14-hydroxy-2-(1-methylethyl)-5,9,13-trimethyl-2,4,8,12-tetradecatetraenoic acid ethyl ester (713 mg, 2.03 mmol) in dry carbon tetrachloride (2 ml) is added triphenylphosphine (787 mg, 3.00 mmol) and the mixture is refluxed with stirring for 2 hours, to confirm whereby the starting compound disappears. After cooling the reaction mixture to room temperature, n-hexane is added to the mixture and insoluble triphenylphosphineoxide is removed by filtration, followed by washing the filtrate with n-hexane. The filtrate and the washing liquid are combined and concentrated. In order to remove a trace amount of triphenylphosphineoxide, to the resulting residue is further added a small amount of n-hexane and the filtration and washing are repeated likewise. The filtrate and the washing liquid are combined and concentrated to give a residue (720 mg, 96%) which is the desired 14-chloro-2-(1-methylethyl)-5,9,13-trimethyl 2,4,8,12-tetradecatetraenoic acid ethyl ester and is usable in the subsequent reaction without further purification.

IR (film) cm$^{-1}$: 1 2960, 2940, 2870, 1710, 1635, 1445, 1385, 1230, 1195, 1145, 1050.

NMR (CDCl$_3$, 250 MHz) δppm: 1.09 (d, J=6.9Hz, 6H, —CH(CH$_3$)$_2$), 1.31 (t, J=7.1Hz, 3H, —CH$_2$CH$_3$), 1.57, 1.70, 1.80 (each bs, each 3H, —C=CCH$_3$), 1.9–2.2 (m, 8H, —CH$_2$CH$_2$—), 2.78(hep, J=6.9Hz, 1H, CH(CH$_3$)$_2$), 3.98 (bs, 2H, —CH$_2$Cl), 4.23(q, J=7.1Hz, 2H, —CH$_2$CH$_3$), 5.1 (m, 1H, —C=CHCH$_2$—), 5.47 (bt, J=6.5Hz, —C=CHCH$_2$—), 6.53 and 6.54 (each bd, J=12.0Hz, each 1H, —C=CH—CH=C—).

EXAMPLE 2

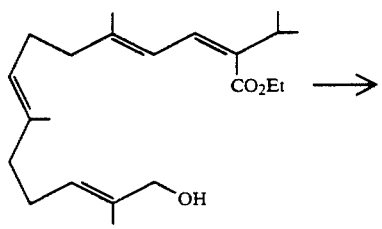

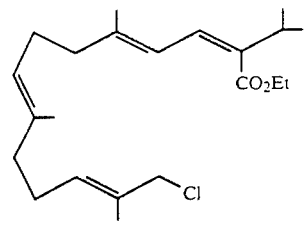

To a mixture of the hydroxyester compound which is 14-hydroxy-2-(1-methylethyl)-5,9,13-trimethyl-2,4,8,12-tetradecatetraenoic acid ethyl ester (71.0 mg, 0.20 mmol), S-collidine (26.7 mg, 0.22 mmol), lithium chloride (8.5 mg, 0.20 mmol) and dimethylformamide (1 ml) is added methanesulfonyl chloride (25.2 mg, 0.22 mmol) under nitrogen atmosphere while stirring on an ice-bath. The stirring is continued at the same temperature for 5 hours. After confirming disappearance of the starting compound, to the reaction mixture are added water and ethyl ether and the organic layer is separated. The organic layer is washed with water, dried (MgSO$_4$) and concentrated. The resulting residue is chromatographed (n-hexane/ethyl acetate =10:1) on silica gel column to give the desired 14-chloro-2-(1-methylethyl)-5,9,13-trimethyl-2,4,8,12-tetradecatetraenoic acid ethyl ester (64.6 mg, 86%) from the desired fraction.

EXAMPLE 3

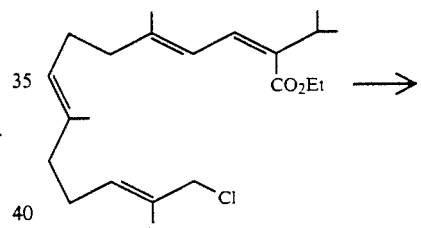

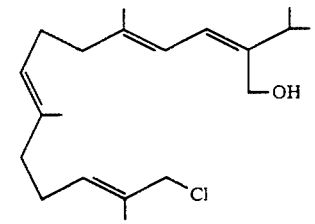

14-Chloro-2-(1-methylethyl)-5,9,13-trimethyl-2,4,8,12-tetradecatetraenoic acid ethyl ester (670 mg, 1.81 mmol) is dissolved in dry toluene (200 ml) under argon atmosphere and to the solution is gradually added a 1 M solution of diisopropylaluminum hydride in toluene (4 ml) while cooling and stirring on ethanol-dry ice bath. After 30 minutes, disappearance of the starting compound is confirmed. To the mixture is added water (1.5 ml), and after removing the bath, the mixture is thoroughly stirred. To the mixture is added a drying agent (anhydrous magnesium sulfate) and the mixture is further stirred. The mixture is filtered and concentrated and the resulting residue is chromatographed (n-hexane/ethyl acetate =12:1) on silica gel column to give the desired alcohol, 14-chloro-2-(1-methylethyl)-5,9,13-trimethyl-2,4,8,12-tetradecatetraene-1-ol (492 mg, 79%) from the desired fraction.

IR (film) cm⁻¹: 3360, 2980, 2940, 2890, 1445, 1385, 1265, 1010.

NMR (CDCl₃, 250 MHz) δppm: 1.06 (d, J=6.8Hz, 6H, —CH(C$\underline{H}$₃)₂), 1.58, 1.70 and 1.75 (each bs, each 3H, —C=CC$\underline{H}$₃), 1.9-2.2 (m, 8H, —C$\underline{H}$₂C$\underline{H}$₂—), 2.47 (hep, J=6.8Hz, 1H, —C$\underline{H}$(CH₃)₂), 3.98 (bs, 2H, —C$\underline{H}$Cl), 4.23 (bs, 2H, —C$\underline{H}$₂OH), 5.09 (m, 1H, —C=C$\underline{H}$CH₂—), 5.47 (bt, J=6.7Hz, —C=C$\underline{H}$CH₂—), 6.13 and 6.16 (each d, J=12.0Hz, each 1H, —C=C$\underline{H}$—C$\underline{H}$=C—).

EXAMPLE 4

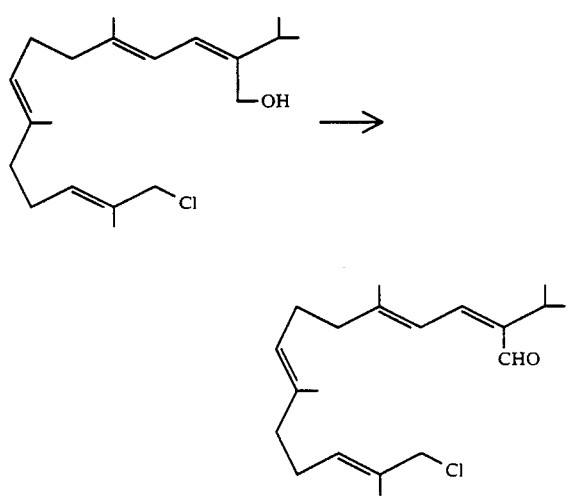

To a solution of the allylalcohol which is 14-chloro-2-(1-methylethyl)-5,9,13-trimethyl-2,4,8,12-tetradecatetraen-1-ol (492 mg, 1.51 mmol) in methylene chloride (22 ml) is added powdered barium manganate (8.5 g) and the mixture is vigorously stirred under argon atmosphere. After 8 hours, disappearance of the starting compound is confirmed and the reaction mixture is filtered and washed. The filtrate and the washing liquid are combined and concentrated. The resulting residue is purified by silica gel column chromatography (n-nexane/ethyl acetate =15:1) to give the desired 14-chloro-2-(1-methylethyl)-5,9,13-trimethyl-2,4,8,12-tetradecatetraenal (468 mg, 95%).

IR (film) cm⁻¹: 2970, 2930, 2880, 1670, 1630, 1445, 1390, 1295, 1265, 1135.

NMR (CDCl₃, 250 MHz) dppm: 1.04 (d, J=7.0Hz, 6H, —CH(C$\underline{H}$₃)₂), 1.59 and 1.70 (each bs, each 3H, —C=CC$\underline{H}$₃), 1.87 (d, J=1.3Hz, 3H, —C=CC$\underline{H}$₃), 1.9-2.2 (m, 8H, —C$\underline{H}$₂C$\underline{H}$₂—), 2.89 (hep, J=7.0Hz, 1H, —C$\underline{H}$(CH₃)₂), 3.98 (bs, 2H, —C$\underline{H}$₂Cl), 5.09 (m, 1H, —C=C$\underline{H}$CH₂—), 5.47 (bt, J=6.5Hz, 1H, —C=C$\underline{H}$C$\underline{H}$₂—), 6.82 (d, J=12.0Hz, 1H, —C=C$\underline{H}$—C$\underline{H}$=C(-CHO)—), 7.11 (d, J=12.0Hz, —C=CH—C$\underline{H}$=C(-CHO)—), 10.27 (s, 1H, —C$\underline{H}$O).

EXAMPLE 5

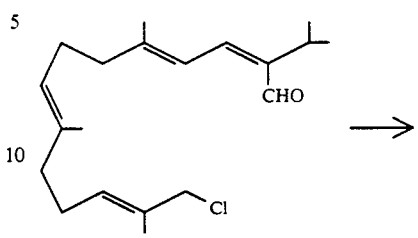

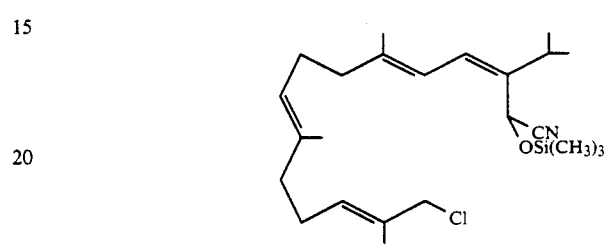

The formyl compound, 14-chloro-2-(1-methylethyl)-5,9,13-trimethyl-2,4,8,12-tetradecatetraenal (468 mg, 1.44 mmol) prepared in Reference Example 4 is dissolved in trimethylsilylnitrile (0.25 ml, 1.87 mmol) and to the solution is added a very small amount of potassium cyanide/18-crown 6-ether complex while stirring under nitrogen atmosphere on an ice-water bath. After 2 hours, disappearance of the starting compound is confirmed and excess of trimethylsilylnitrile is removed by distillation to give 15-chloro-3-(1-methylethyl)-6,10,14-trimethyl-2-(trimethylsiloxy)-3,5,9,13-pentadecatetraenenitrile (610 mg, quantitative).

IR (film) cm⁻¹: 2960, 2930, 2880, 2320, 1445, 1255, 1080, 875, 845.

NMR (CDCl₃, 250 MHz) δppm: 1.11 and 1.15 (each d, J=6.9Hz, each 3H, —CH(C$\underline{H}$₃)₂), 1.60, 1.71 and 1.77 (each s, each 3H, —C=CC$\underline{H}$₃), 1.9-2.2 (m, 8H; —C$\underline{H}$₂C$\underline{H}$₂—), 2.64 (hep, J=6.9Hz, 1H, —C$\underline{H}$(CH₃)₂), 3.99 (s, 1H, —C$\underline{H}$₂Cl), 5.11 (m, 1H, —C=C$\underline{H}$CH₂—), 5.33 (s, 1H, —C$\underline{H}$CN), 5.48 (bt, J=6.5Hz, 1H, —C=C$\underline{H}$CH₂—), 6.04 and 6.25 (each d, J=11.3Hz, each 1H, —C=C$\underline{H}$—C$\underline{H}$=C—).

EXAMPLE 6

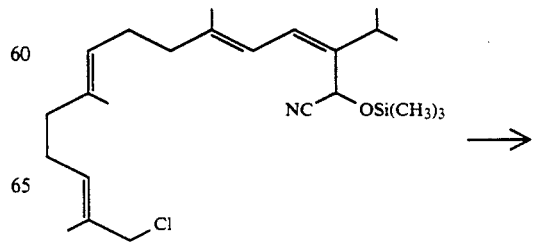

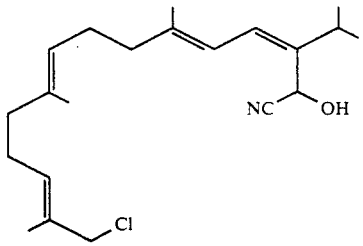

To a solution of 15-chloro-3-(1-methylethyl)-6,10,14-trimethyl-2-trimethylsiloxy-3,5,9,13-pentadecatetraenenitrile (58 mg, 0.14 mmol) prepared in Reference Example 5 in tetrahydrofuran (2 ml) cooled at 0° C. is slowly added 1N hydrochloric acid (0.5 ml). After stirring at this temperature for 10 minutes, to the mixture is added a saturated saline solution (5 ml) and the mixture is extracted with ether (10 ml×2). The organic layer is washed with a saturated saline solution (5 ml) and dried over anhydrous sodium sulfate. The solvent is removed by distillation under reduced pressure and the resulting residue is purified by silica gel column chromatography (n-hexane/ethyl acetate =10:1) to give 15-chloro-2-hydroxy-3-(1-methylethyl)-6,10,14-trimethyl-3,5,9,13-pentadecatetraenenitrile (38 mg, 75%).

IR (film) cm$^{-1}$: 3450, 2960, 2930, 2875, 2860, 2320, 1650, 1445, 1385, 1265, 1020, 930.

NMR (CDCl$_3$, 250 MHz) δppm: 1.14 and 1.28 (each d, J=6.8Hz, each 3H, CH(CH$_3$)$_2$), 1.59, 1.71 and 1.79 (each s, each 3H, —C=CCH$_3$), 1.90-2.20 (m, 8H, —CH$_2$CH$_2$—), 2.27 (d, J=5.5Hz, 1H, OH), 2.62 (hep, J=6.8Hz, 1H, CH$_2$(CH$_3$)2), 3.99 (s, 2H, —CH$_2$Cl), 5.09 (m, 1H, —C=CH—CH$_2$—), 5.29 (d, J=5.5Hz, 1H, CHCN), 5.48 (br t, J=6.4Hz, 1H, —C=CHCH$_2$—), 6.14 and 6.34 (each d, J=11.4, 11.5Hz, each 1H, —C=CH—CH=C—).

EXAMPLE 7

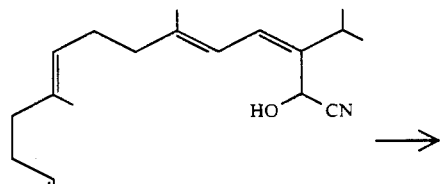

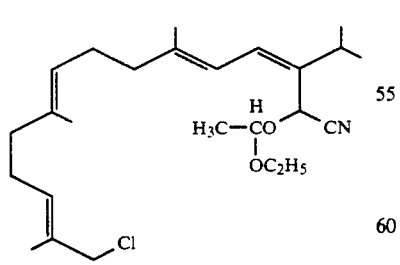

To a solution of 15-chloro-2-hydroxy-3-(1-methylethyl)-6,10,14-trimethyl-3,5,9,13 pentadecatetraenenitrile (204 mg, 0.56 mmol) prepared in Reference Example 6 and ethyl vinyl ether (100 μl, 0.96 mmol) in dichloromethane (5 ml) is added a very small amount of paratoluenesulfonic acid while stirring under nitrogen atmosphere on an ice-water bath. After 10 minutes, to the mixture are added a saturated aqueous sodium hydrogencarbonate solution (15 ml) and n-hexane/ether (1:1) solution (20 ml) and the organic layer is separated. The aqueous layer is then extracted with n-hexane/ether (1:1) solution (20 ml) for several times. The organic layers are combined and dried over anhydrous sodium sulfate and the solvent is removed by distillation under reduced pressure. The resulting residue is purified by silca gel column chromatography (n-hexane/ethyl acetate =20:1) to give 15-chloro-2-(1-ethoxyethoxy)3-(1-methylethyl)-6,10,14-trimethyl-3,5,9,13-pentadecatetraenenitrile (207 mg, 85%).

IR (film) cm$^{-1}$: 2960, 2930, 1445, 1385, 1262, 1140, 1080, 1050, 1020, 930.

NMR (CDCl$_3$, 250 MHz) δppm: 1.06-1.25 (m, 9H, CH$_3$CH$_2$O, CH(CH$_3$)$_2$), 1.35 and 1.38 (each d, J=5.5 7.9Hz, 3H, CH$_3$CHO), 1.58, 1.70 and 1.77 (each s, each 3H, —C=CCH$_3$), 1.90-2.30 (m, 8H, —CH$_2$CH$_2$—), 2.60 (hep, J=6.8Hz, 1H, CH(CH$_3$)$_2$), 3.45-3.74 (m, 2H, OCH$_2$CH$_3$), 3.98 (s, 2H, CH$_2$Cl), 4.77 and 4.99 (each q, J=5.5Hz, 1H, OCHCH$_3$), 5.10 (br s, 1H, —C=CH—CH$_2$—), 5.29 and 5.34 (each s, 1H, CHCN), 6.09 (d, J=11.4Hz, 1H, —C=CH=CH=C—), 6.32 and 6.35 (each d, J=11.4Hz, 1H, —C=CH—CH=C—).

EXAMPLE 8

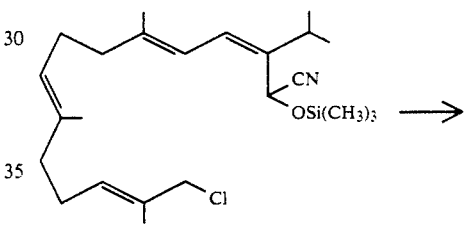

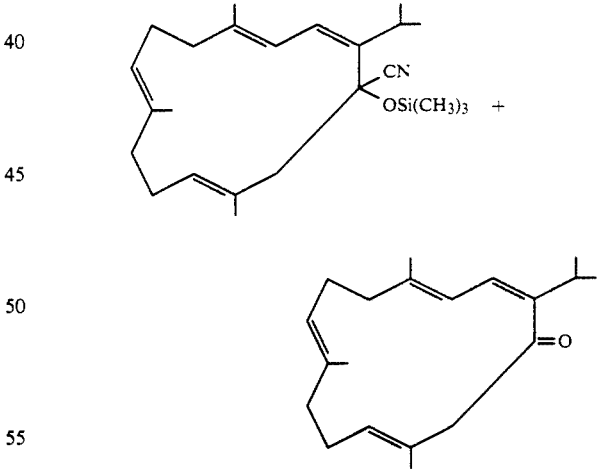

A solution of lithium bis(trimethylsilyl) amide (5.0 mmol, 0.25 M) in dry tetrahydrofuran (20 ml) is stirred under argon atmosphere on an oil bath at 40° C. and thereto is dropwise added a solution of the cyanohydrin trimethylsilyl ether which is 15-chloro-3-(1-methylethyl)-6,10,14-tri-methyl-2-trimethylsiloxy-3,5,9,13-pentadecatetraenenitrile (378 mg, 0.895 mmol) prepared in Reference Example 5 in dry tetrahydrofuran (15 ml) over 50 minutes. After stirring the mixture at this temperature for 20 minutes, the reaction is quenched by adding a saturated aqueous ammonium chloride solution while stirring on an ice-water bath. After removing tetrahydrofuran by distillation under reduced pressure, the organic layer is extracted with ether. The obtained extract is purified by silica gel column chromatography (n-hexane/ethyl acetate =60:1) to give 2-(1-methylethyl)-5,9,13-trimethyl-1-trimethylsiloxy-2,4,8,12-cyclotetradecatetraene-1-carbonitrile (288 mg, 83%) and 2-(1-methylethyl)-5,9,13-trimethyl-2,4,8,12-cyclotetradeca-tetraen-1-on (42.9 mg, 16%).

The following NMR data are obtained for 2-(1-methylethyl)-5,9,13-trimethyl-1-trimethylsiloxy-2,4,8,12-cyclotetradecatetraene-1-carbonitrile.

NMR (CDCl$_3$, 250 MHz) δppm: 0.23 (s, 9H, —Si(CH$_3$)$_3$), 1.09 and 1.15 (each d, J=6.7Hz, each 3H, —CH(CH$_3$)$_2$), 1.50 and 1.62 (each bs, each 3H, —C=CCH$_3$), 1.70 (d, J=1.3Hz, 3H, —C=CCH$_3$), 2.0–2.2 (m, 8H, —CH$_2$CH$_2$—), 2.51 (hep, J=6.7Hz, 1H, —CH(CH$_3$)$_2$), 2.55 and 2.65 (each d, J=14.2Hz, each 1H, —CH$_a$ H$_b$CN—), 4.94 (bt, J=6.1Hz, 1H, —C=CHCH$_2$—), 5.15 (bt, J=5.6Hz, 1H, —C=CHCH$_2$—), 6.17 and 6.44 (each d, J=11.8Hz, each 1H, —C=CH—CH=C—).

EXAMPLE 9

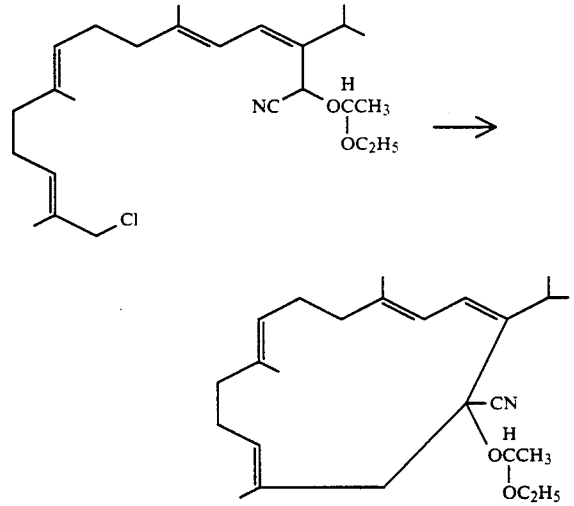

A solution of hexamethyldisilazane lithium amide (205 mg, 1.11 mmol) in dry hexane/benzene (1:4) solution (5 ml) is stirred on an oil bath at 90° C. and thereto is dropwise added a solution of cyanohydrin ethoxyethyl ether which is 15-chloro-2-(1-ethoxyethoxy)-3-(1-methylethyl)-6, 10,14-trimethyl-3,5,9,13-pentadecatetraenenitrile (115 mg, 0.26 mmol) in dry benzene (6 ml) over 20 minutes. After stirring the mixture at this temperature for 5 minutes, a saturated aqueous ammonium chloride solution is added while stirring on an ice-water bath. The organic layer is extracted with ether (20 ml×2) and the solvent is removed by distillation under reduced pressure to give 1-(1-ethoxyethoxy)-2-(1-methylethyl)-5,9,13-trimethyl-2,4,8,12 -cyclotetradecatetraene-1-carbonitrile (51.6 mg, 50%) as a mixture of diastereomers. This product is subjected to silica gel column chromatography (n-hexane/ether =20:1) to give one isomer of the above formula.

IR (film) cm$^{-1}$: 2975, 2940, 1450, 1385, 1140, 1025, 940.

NMR (CDCl$_3$, 250 MHz) δppm: 1.10 and 1.14 (each d, J=6.7Hz, each 3H, CH(CH$_3$)$_2$), 1.22 (t, J=7.1Hz, 3H, CH$_3$CH$_2$O), 1.28 (d, J=5.4Hz, 3H, CH$_3$CHO), 1.49, 1.68 and 1.71 (each s, each 3H, CH$_3$—C=C—), 1.95–2.28 (m, 8H, CH$_2$—C=C—), 2.60 (hep, 1H, J=6.7Hz, CH(CH$_3$)$_2$), 2.72 and 2.89 (each d, J=14.7Hz, each 1H, CH$_a$CH$_b$CCN), 3.58 (q, J=7.1Hz, 2H, OCH$_2$CH$_3$), 4.89 (q, J=5.4Hz, 1H, —OCH—CH$_3$), 4.86–5.00 and 5.06–5.18 (each m, each 1H, —CH—CH$_2$—), 6.28 (br s, 2H, —C=CH—CH=C—).

EXAMPLE 10

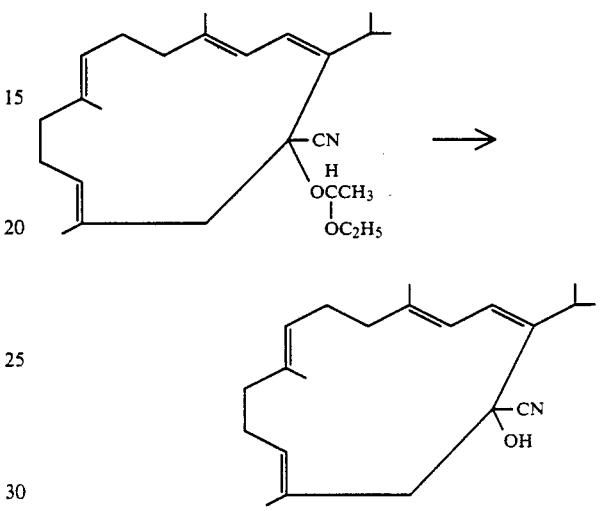

A solution of 1-(1-ethoxyethoxy)-2-(1-methylethyl)-5,9,13-trimethyl-2,4,8,12-cyclotetradecatetraene-1-carbonitrile (31.8 mg, 0.08 mmol) prepared in Example 1 in methanol (3 ml) is stirred on an ice-water bath and thereto is added a very small amount of paratoluenesulfonic acid. After stirring the mixture at this temperature for 1 hour, a saturated aqueous sodium chloride solution (3 ml) is added and the mixture is extracted with ether (10 ml×2). The solvent is removed by distillation under reduced pressure and the resulting residue is purified by silica gel column chromatography (n-hexane/ethyl acetate =7:1) to give 2-(1-methylethyl)-5,9,13-trimethyl-2,4,8,12-cyclotetradecatetraene-1-carbonitrile (13.7 mg, 60%).

NMR (CDCl$_3$, 250 MHz) δppm: 1.15 and 1.19 (each d, J=6.7Hz, each 3H, CH(CH$_3$)$_2$), 1.55, 1.63 and 1.69 (each s, each 3H, CH$_3$—C=C—), 1.94–2.35 (m, 8H, CH$_2$—C=C—), 2.51 (hep, J=6.7Hz, 1H, CH(CH$_3$)$_2$), 2.66 and 2.73 (each d, J=14.1Hz, 2H, CH$_a$ H$_b$CCN), 2.89 (br s, 1H, OH), 4.93 and 5.24 (each br t, J=5.3Hz, each 1H, —C=CH—CH$_2$—), 6.22 and 6.42 (each d, J=11.1Hz, each 1H, —C=CH—CH=C—).

EXAMPLE 11

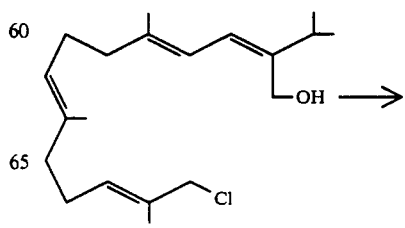

-continued

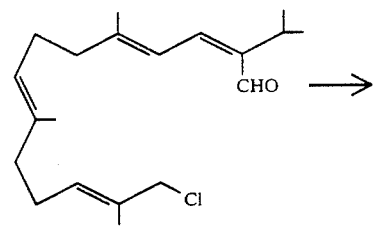

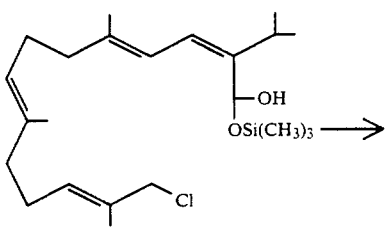

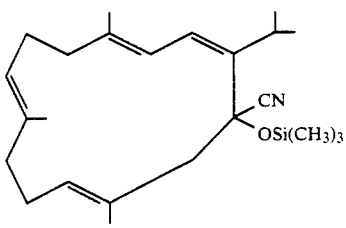

To a solution of the alcohol compound which is 14-chloro-2-(1-methlethyl)-5,9,13-trimethyl-2,4,8,12-tetradecatetraen-1-ol (453 mg. 1.66 mmol) in methylene chloride (25 ml) is added powdered barium manganate (6.5 g) under argon atmosphere and the mixture is stirred at room temperature for 24 hours. The reaction mixture is filtered and washed with methylene chloride. The combined methylene chloride layers are concentrated under reduced pressure. The resulting residue (crude formyl compound) is dissolved in trimethylsilylnitrile (0.29 ml, 2.16 mmol) under nitrogen atmosphere and to the solution is added a very small amount of potassium cyanide/18-crown 6-ether complex while stirring on an ice-water bath. After 2 hours, the excess trimethylsilylnitrile is removed by distillation to give a residue (563 mg). The obtained crude cyanohydrin ether is dissolved in dry tetrahydrofuran (22 ml) and the solution is dropwise added to a 1 M solution of lithium bis(trimethylsilyl)amide in tetrahydrofuran (4.0 ml), said solution being diluted with dry tetrahydrofuran (22 ml), at 50° C. to 52° C. over 35 minutes under argon atmosphere. After completion of dropwise addition, tetrahydrofuran is immediately removed by distillation under reduced pressure and the resulting residue is dissolved in a mixture of diethyl ether and cooled 1 N hydrochloric acid (30 ml). The ether layer is washed with water, dried (MgSO$_4$) and concentrated. The resulting residue is subjected to silica gel column chromatography (eluent: n-hexane/ethyl acetate =30:1) to give the desired 2-(1-methylethyl)-5,9,13-trimethyl-1-trimethylsiloxy 2,4,8,12-cyclotetradecatetraene-1-carbonitrile (330 mg, 64%, calculated from the starting alcohol).

REFERENCE EXAMPLE 1

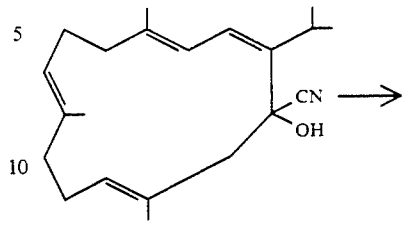

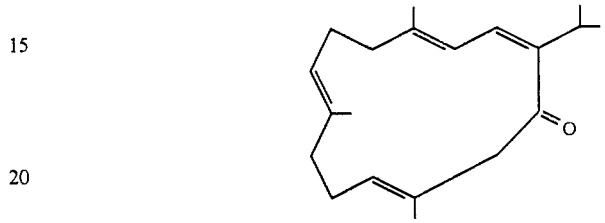

A solution of the cyanohydrin which is 1-hydroxy-2-(1-methylethyl)-5,9,13-trimethyl-2,4,8,12-cyclotetradecatetraenecarbonitrile (78.0 mg, 0.25 mmol) in ethyl ether (4 ml) is added to a saturated aqueous sodium hydrogen carbonate solution (2 ml) on an ice-water bath and the mixture is stirred for 10 minutes under nitrogen atmosphere. After confirming disappearance of the starting compound, the organic layer is washed with water, dried over anhydrous magnesium sulfate and concentrated. The resulting residue is subjected to silica gel column chromatography (eluent: n-hexane/ethyl acetate =7:1) to give the desired ketone, 2-(1-methylethyl)-5,9,13-trimethyl-2,4,8,12-cyclotetradecatetraen-1-on (58.0 mg, 75%).

REFERENCE EXAMPLE 2

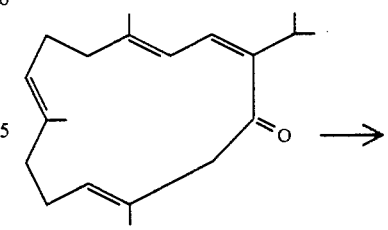

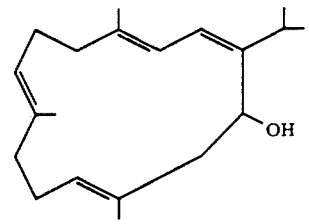

Under argon atmosphere, to a solution of the ketone, 2-(1-methylethyl)-5,9,13-trimethyl-2,4,8,12-cyclotetradecatetraen-1-on (137 mg, 0.48 mmol) prepared in Reference Example 8 in dry toluene (25 ml) is dropwise added a 1 M solution of diisobutylaluminum hydride in toluene (0.6 ml) while stirring on a refrigerant bath at −70° C. After 1 hour, disappearance of the starting compound is confirmed. To the mixture is added water (0.25 ml) and the mixture is stirred enough after removing the bath. The mixture is dried over anhydrous magnesium sulfate, stirred, filtered and concentrated. The resulting residue is purified by silica gel column chromatography (eluent: n-hexane/ethyl acetate =12:1) to give the desired Sarcophytol A (125 mg, 88%).

REFERENCE EXAMPLE 3

Under argon atmosphere, to lithium aluminum hydride (80.0 mg, 2.11 mmol) is added diethyl ether (5 ml) and the mixture is stirred and to the suspension is dropwise added a solution of (1R, 2S)-(−)-N-methylephedrine (380 mg, 2.12 mmol) in diethyl ether (5 ml) at room temperature over 5 minutes. After refluxing with stirring for 1 hour, N-ethylaniline (0.53 ml, 4.23 mmol) is dropwise added to the mixture over 5 minutes and the mixture is refluxed for additional 1 hour while stirring. The reaction mixture is cooled to −72° C., thereto is slowly dropwise added a solution of the ketone (136 mg, 0.475 mmol) prepared in Reference Example 8 in diethyl ether (3 ml) and the mixture is stirred at −72° C. for 6 hours. After 1 N hydrochloric acid (9 ml) is added to the mixture, the organic layer is separated, washed with 3 N hydrochloric acid (5 ml×2) and dried over anhydrous sodium sulfate. The solvent is removed by distillation under reduced pressure and the resulting residue is subjected to silica gel column chromatography to give optically active Sarcophytol A (80 mg, 60%) and unreacted ketone (51 mg, 37%).

The obtained optically active Sarcophytol A showed an optical purity of 87% by high performance liquid chromatography (HPLC) analysis using an optical isomer separation column (CHIRALCELL OD manufactured by Dicel Chemical Industry K.K.).

REFERENCE EXAMPLE 4

Under argon atmosphere, to a solution of lithium aluminum hydride in diethyl ether (2.26 ml, 1.40 mmol, 0.62 M) is dropwise added a solution of (S)-2-(anilinomethyl)-pyrrolidine (296 mg, 1.68 mmol) in diethyl ether (3 ml) while stirring at room temperature over 10 minutes. The reaction mixture is stirred for additional 1 hour and then cooled to −72° C. To the mixture is slowly dropwise added a solution of the ketone (162 mg, 0.56 mmol) prepared in Reference Example 8 in diethyl ether (5 ml). After the mixture is stirred at −72° C. for 1 hours, a saturated aqueous sodium sulfate solution (1 ml) and the mixture is stirred at room temperature for 10 minutes. 1 N Hydrochloric acid (15 ml) and diethyl ether (20 ml) are added to the mixture and the organic layer is separated. The aqueous layer is extracted with diethyl ether (20 ml), washed with a saturated saline solution (20 ml), dried over anhydrous sodium sulfate and the solvent is removed by distillation under reduced pressure. The resulting residue is purified by silica gel column chromatography to give the desired optically active Sarcophytol A (126 mg, 78%).

The obtained optically active Sarcophytol A showed an optical purity of 92% by high performance liquid chromatography (HPLC) analysis using an optical isomer separation column (CHIRALCELL OD manufactured by Dicel Chemical Industry K.K.).

$[\alpha]^{24}_D = +209.9°$ (c=0.372, CHCl$_3$)

REFERENCE EXAMPLE 5

Under argon atmosphere, to a solution of lithium aluminum hydride in diethyl ether (2.94 ml, 2.0 mmol, 0.68 M) is slowly dropwise added (S)-2-(2,6-xylidinomethyl)-pyrrolidine (490 mg, 2.4 mmol) while stirring at room temperature. After completion of the dropwise addition, the reaction mixture is stirred at room temperature for 2 hours. The reaction mixture is cooled to −72° C. and thereto is dropwise added a solution of the ketone (69 mg, 0.24 mmol) prepared in Reference Example 8 in diethyl ether (3 ml) over 10 minutes. After stirring at −74° C. for 1 hour, a saturated aqueous sodium sulfate solution (1 ml) is added and the mixture is stirred at room temperature for a while. Diethyl ether (10 ml) and diluted hydrochloric acid (20 ml) are added to the mixture, the organic layer is separated and the aqueous layer is extracted with diethyl ether (20 ml). The extract is washed with a saturated saline solution (20 ml), dried over anhydrous sodium sulfate and the solvent is removed by distillation under reduced pressure. The resulting residue is purified by silica gel column chromatography to give optically active Sarcophytol A (61 mg, 88%).

The obtained optically active Sarcophytol A showed an optical purity of 93% by high performance liquid chromatography (HPLC) analysis using an optical isomer separation column (CHIRALCELL OD manufactured by Dicel Chemical Industry K.K.).

$[\alpha]^{24}_D = +204.4°$ (c=0.27, CHCl$_3$)

REFERENCE EXAMPLE 6

Under argon atmosphere, a suspension of tin (II) chloride (382 mg, 2.01 mmol) and (R)-1-methyl-2-(piperidinomethyl)pyrrolidine (366 mg, 2.01 mmol) in dichloromethane (6 ml) is cooled to −72° C. and thereto is added a solution of diisobutylaluminum hydride in toluene (1.0 mmol) and the mixture is stirred for 10 minutes. To the mixture is slowly dropwise added a solution of the ketone (100 mg, 0.349 mmol) prepared in Reference Example 8 in dichloromethane (3 ml) at −72° C. After stirring the reaction mixture for 4 hours, a saturated saline solution (3 ml) is added and the mixture is stirred at room temperature for 30 minutes. The precipitate is removed by filtration with Celite, the filtrate is dried over anhydrous sodium sulfate and the solvent is removed by distillation under reduced pressure. The resulting residue is purified by silica gel column chromatography to give optically active Sarcophytol A (79.2 mg, 79%).

The obtained optically active Sarcophytol A showed an optical purity of 42% by high performance liquid chromatography (HPLC) analysis using an optical isomer separation column (CHIRALCELL OD manufactured by Dicel Chemical Industry K.K.).

$[\alpha]^{25}_D = +101.9°$ (c=0.54, CHCl$_3$)

What is claimed is:

1. A monocyclic terpene derivative of the formula:

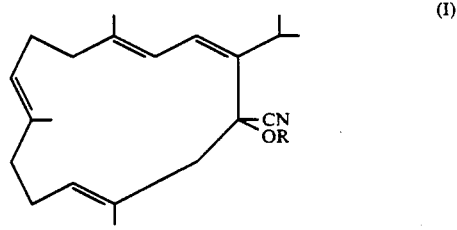

(I)

wherein R is hydrogen atom, trimethylsilyl group or 1-ethoxyethyl group.

2. The compound according to claim 1, wherein R is hydrogen atom.

3. The compound according to claim 1, wherein R is trimethylsilyl group.

4. The compound according to claim 1, wherein r is ethoxyethyl group.

5. A process for preparing the compound of the formula (I)

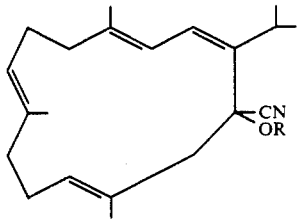
(I)

wherein R is hydrogen, trimethylsilyl or 1-ethoxyethyl which comprises reacting a compound of the formula:

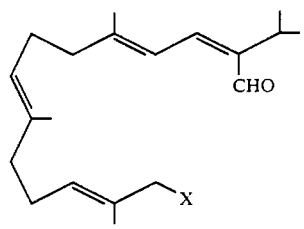
(D)

wherein X is halogen atom or a group of the formula: $-OSO_2R^1$ wherein $R^1$ is a lower ($C_{1-4}$) alkyl group which may be substituted by a halogen atom or a phenyl group which may be substituted by a lower ($C_{1-4}$) alkyl group, with trimethylsilylnitrile in the presence of a catalytic amount of metal cyanide-18-crown6-ether complex to give a compound of the formula (E):

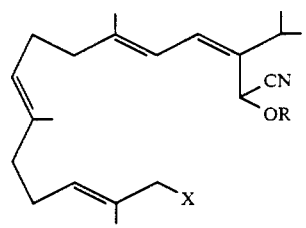
(E)

wherein R is trimethylsilyl, and reacting the compound (E) with a base.

6. A process for preparing the compound of the formula (I)

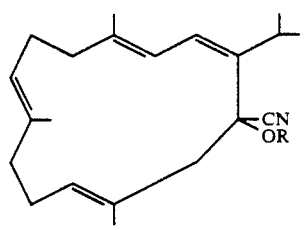
(I)

wherein R is hydrogen, trimethylsilyl or 1-ethoxyethyl which comprises reacting a compound of the formula:

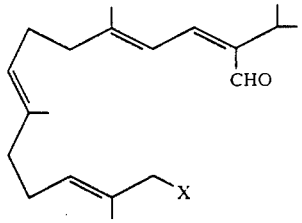
(D)

wherein X is halogen atom or a group of the formula: $-OSO_2R^1$ wherein $R^1$ is a lower ($C_{1-4}$) alkyl group which may be substituted by a halogen atom or a phenyl group which may be substituted by a lower ($C_{1-4}$) alkyl group, with trimethylsilylnitrile in the presence of a catalytic amount of metal cyanide-18-crown-6-ether complex to give a compound of the formula (E):

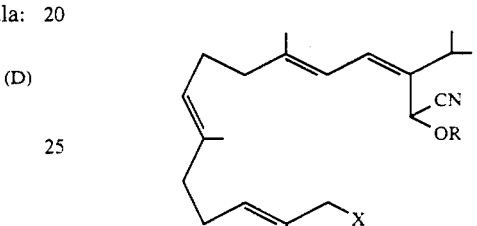
(E)

wherein R is trimethylsilyl, reacting the first intermediate (E) with a mineral acid or a tetraalkylammonium compound to give the second intermediate of the formula (E) wherein R is hydrogen, and reacting the second intermediate with a base.

7. A process for preparing the compound of the formula (I)

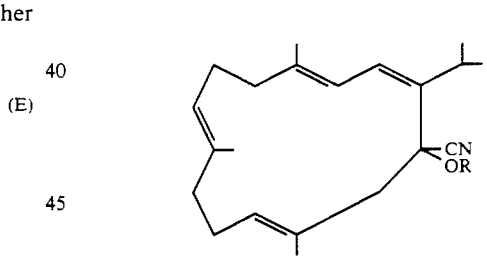
(I)

wherein R is hydrogen, trimethylsilyl or 1-ethoxyethyl which comprises reacting a compound of the formula:

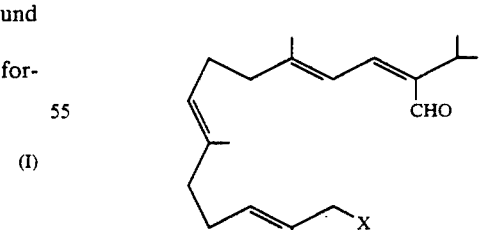
(D)

wherein X is halogen atom or a group of the formula: $-OSO_2R^1$ wherein $R^1$ is a lower ($C_{1-4}$) alkyl group which may be substituted by a halogen atom or a phenyl group which may be substituted by a lower ($C_{1-4}$)alkyl group, with trimethylsilylnitrile in the presence of a catalytic amount of metal cyanide-18-crown-6-ether complex to give a compound of the formula (E):

21

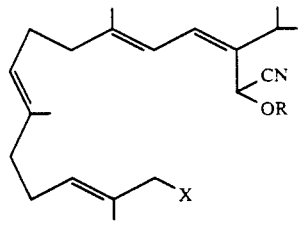

(E)

wherein R is trimethylsilyl, reacting the first intermediate (E) with a mineral acid or a tetraalkylammonium compound to give the second intermediate of the formula (E) wherein R is hydrogen, reacting the second intermediate with ethyl vinyl ether to give the third intermediate of the formula (E) wherein R is ethoxyethyl, and reacting the third intermediate with a base.

* * * * *

22

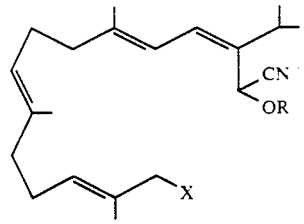

(E)

wherein R is trimethylsilyl, reacting the first intermediate (E) with a mineral acid or a tetraalkylammonium compound to give the second intermediate of the formula (E) wherein R is hydrogen, reacting the second intermediate with ethyl vinyl ether to give the third intermediate of the formula (E) wherein R is ethoxyethyl, and reacting the third intermediate with a base.

* * * * *